United States Patent
Davis et al.

(10) Patent No.: US 6,800,739 B2
(45) Date of Patent: Oct. 5, 2004

(54) ISOLATION OF GLYCOPROTEINS FROM BOVINE MILK

(75) Inventors: Martin E. Davis, Tonka Bay, MN (US); Fang Ming, Madison Lake, MN (US); Mengyan Yang, Le Sueur, MN (US); Akimoto Ichinomiya, Tokushima (JP); Sharyn X. Su, Plymouth, MN (US); Nicholas Melachouris, Laguna Nigel, CA (US)

(73) Assignee: Davisco Foods International, Inc., Le Sueur, MN (US)

( * ) Notice: Subject to any disclaimer, the term of this patent is extended or adjusted under 35 U.S.C. 154(b) by 208 days.

(21) Appl. No.: 10/116,968

(22) Filed: Apr. 5, 2002

(65) Prior Publication Data

US 2003/0045677 A1 Mar. 6, 2003

Related U.S. Application Data

(60) Provisional application No. 60/281,816, filed on Apr. 5, 2001.

(51) Int. Cl.[7] .............................................. C07K 1/00
(52) U.S. Cl. ..................................................... 530/395
(58) Field of Search ............................... 530/395, 350; 514/8, 12, 21

(56) References Cited

U.S. PATENT DOCUMENTS

| | | | | |
|---|---|---|---|---|
| 4,108,849 A | * | 8/1978 | Thomas ...................... | 530/395 |
| 5,118,516 A | * | 6/1992 | Shimatani et al. .......... | 426/271 |
| 5,216,129 A | * | 6/1993 | Berrocal et al. ............ | 530/360 |

* cited by examiner

Primary Examiner—Karen Cochrane Carlson
Assistant Examiner—Sheridan K Snedden
(74) Attorney, Agent, or Firm—Kagan Binder, PLLC

(57) ABSTRACT

A process isolates and recovers glycoprotein fractions in dry or solution form. Glycoproteins are recovered from deproteinized whey, preferably micro-filtered to remove large molecules and aggregates. The resulting retentate is then diluted for further processing. The resulting liquid is heated to coagulate whey protein and then cooled sufficiently to precipitate coagulated whey protein. The preparation can then be completed by centrifuging the resulting cooled solution and separating resulting supernatant containing glycoproteins from fat and precipitate. The product glycoprotein concentrate can be dried, such as by freeze drying, or recovered and stored in liquid form. In a preferred aspect, saline is employed to dilute the microfiltered concentrate prior to heating to improve the recovery of a liquid glycoprotein fraction that can be sterilized, such as by autoclaving. In another aspect, glycoprotein free of a majority of glycomacropeptides (GMP) can be recovered by adjusting the solution to alkaline pH and subjecting to ion exchange extraction. Preferred liquid products are stable to autoclaving and free of separation after storage in a sealed container at 20° C. for a period of at least one month.

17 Claims, 4 Drawing Sheets

4-15% SDS page. PAS stained
Lane 1 and lane 2 is the glycoprotein preparation from example 2 and 3.

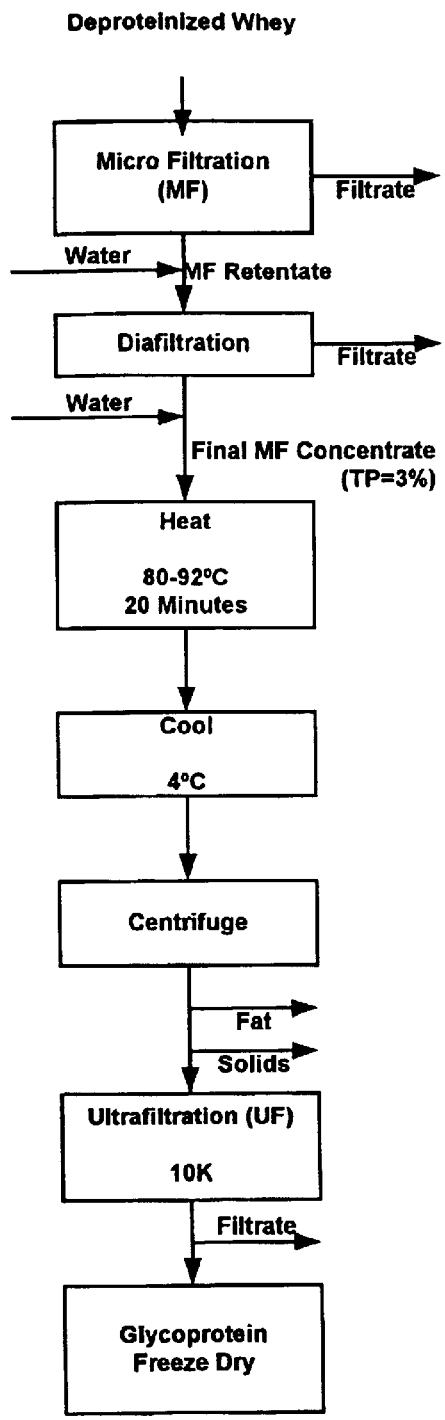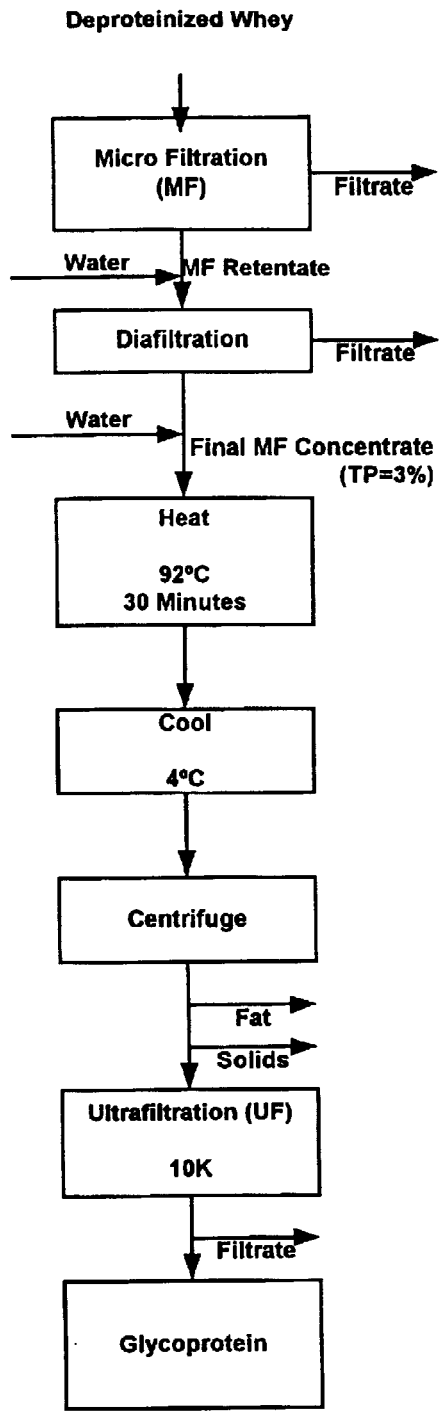

ISOLATION OF GLYCOPROTEINS FROM BOVINE MILK

This application claims the benefit of provisional application Ser. No. 60/281,816 filed Apr. 5, 2001.

BACKGROUND OF THE INVENTION

The invention provides simple and economic methods to isolate glycoproteins (containing mucin, including MUC1) from whey or whey byproducts for the food, pharmaceutical, cosmetic, and other industries. The invention enables a simple recovery of glycoprotein concentrates having excellent thermal stability and solution clarity from whey recovered from cheese production from bovine milk.

Glycoproteins have received attention as a functional additive in various health care and other formulations. It has, for example proved useful as a lubricant in eye care compositions.

The production of cheese from bovine milk results in the production of large amounts of whey. Liquid whey is a complex mixture of protein, fat and salt components in various physical forms and typically has a total solids content of around 6% and contains about 94% water. Lactose can typically be present at a concentration above 4%, lactic acid about 0.2%, ash about 0.5% and fat about 0.15%. Whey protein (total nitrogen times 6.38) is under 1%. The separation of the glycoprotein components from whey, while maintaining recovery of other useful components, presents a technical challenge. Doing this on a large, commercial scale presents an even greater challenge.

Whey is useful in all of its forms. In some cases whey is processed to directly recover whey protein and leaves behind a material often referred to as deproteinized whey, which refers to the liquid remaining after treatment of whey to remove the majority of the whey protein. The material is not deproteinized completely, but contains most of the insoluble membrane protein fragments from milk fat globular membrane (MFGM) originally present in the whey. When produced by some procedures, the fat content is essentially removed. In others, such as ion exchange chromatography, the fat is not removed and is carried along with the deproteinized whey and contains proteins associated with the fat. This fraction contains most of the insoluble membrane fragments.

Bovine MFGM contains considerable amounts of glycoproteins including mucins such as MUC1 and other glycoproteins useful in a variety of food, pharmaceutical, cosmetic, and other products. There are at least five glycoproteins associated with MFGM that can be seen on SDS-gel and can also be detected in membrane concentrated whey. They are MUC1, PASIII, CD36, BTN, and PAS 6/7 according to Mather (2000).

The recovery of glycoproteins could be improved for many applications by providing solutions with high purity, clarity, stability in the presence of salt (e.g., for isotonic or buffered solutions) and heat stability. Accordingly, there is a need for a process that can recover and purify and isolate the various glycoproteins, especially in stable forms for applications requiring either dry or solution formulations.

BRIEF DESCRIPTION OF THE INVENTION

It is an objective of the invention to provide methodology suitable for obtaining useful glycoproteins containing mucin, including MUC1, from whey.

It is another object of the invention to enable the production of glycoproteins in suitable quantities and of suitable quality for supply to the food, pharmaceutical, cosmetic, and other industries.

It is another object of the invention to improve the overall cheese making process by recovering valuable glycoproteins from whey in a manner that permits most whey protein to be separated from the whey prior to concentrating and recovering glycoproteins from bovine MFGM present in the whey.

It is another object of the invention to provide a simple process that produces glycoprotein concentrates suitable for a variety of uses requiring stability.

It is another, specific object of the invention to provide a simple process that produces glycoprotein concentrates that can be packaged as sterile, clear liquids.

It is another object of the invention to provide a simple process that produces glycoprotein concentrates suitable for a variety of uses requiring stability in solution form that can undergo autoclaving to achieve sterility.

These and other objects are accomplished by the present invention by several procedures.

In one aspect, purified glycoprotein fractions are separated from bovine whey, by: diluting microfiltered deproteinized whey protein to solubilize lactose and mineral salts; heating the resulting diluted aqueous micro-filtered deproteinized whey protein to coagulate heat-sensitive whey protein; cooling the resulting heated solution to precipitate coagulated whey protein; and centrifuging the resulting cooled solution and separating resulting supernatant containing glycoproteins from fat and precipitate.

The product glycoprotein concentrate can be dried, such as by freeze drying, or recovered and stored in liquid form. In a preferred aspect, saline is employed to dilute the microfiltered concentrate prior to heating to improve the recovery of a liquid glycoprotein fraction that can be sterilized, such as by autoclaving. In another aspect, glycoprotein free of a majority of glycomacropeptides (GMP) can be recovered by adjusting the solution to alkaline pH and subjecting to ion exchange extraction.

Some preferred aspects of the invention are set forth below and in the attached flow diagrams.

BRIEF DESCRIPTION OF THE DRAWINGS

The invention will be better understood and its advantages will become more apparent when the following detailed description is read in conjunction with the accompanying drawings, wherein:

FIG. 5 is a flow diagram of a process for isolating and recovering a dried glycoprotein fraction.

FIG. 6 is a flow diagram of a process for isolating and recovering a liquid glycoprotein fraction.

DETAILED DESCRIPTION OF THE INVENTION

Figure 1:
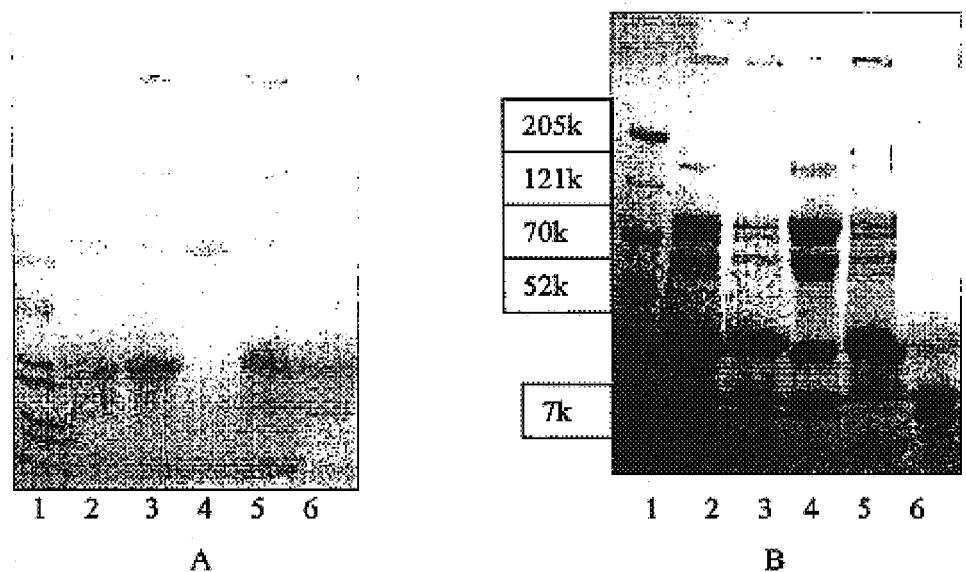
FIG. 1 is a photograph of slide panels showing SDS PAGE electrophoresis utilizing 4–15% gradient gels indicating the presence of glycoproteins. Panels A and B are the same gel, which is stained first with PAS, which is specific for glycoprotein (A) and later with Coomassie blue (B). Lane 1, shows molecular weight standards, from top: 205, 121, 70, 52, 34, 29, 16, 7 kd; lane 2, MF retentate as stated in Example 1; lane 3, glycoprotein preparation as stated in Example 1; lane 4, precipitates of MFGM fraction after heating to 92° C. as stated in Example 1; lane 5, glycoprotein as stated in Example 4; lane 6, 1M sodium chloride eluate of QAE adsorbed proteins.

The invention improves processing for recovering glycoproteins and the quality of solutions of them. The invention provides simple processing that enables the production of these glycoproteins from bovine milk. The products are stable in dry and liquid forms, and in preferred form the solutions can be sterilized by autoclaving to permit packaging without the need for antimicrobials.

One of the principal advantages of the invention is the provision of simple and practical processing for recovering glycoproteins from whey resulting from the production of cheese from bovine milk. Bovine whey, typically liquid whey, is a complex mixture of protein, fat and salt components in various physical forms and typically has a total solids content of around 6% and contains about 94% water. Lactose can typically be present at a concentration above 4%, lactic acid about 0.2%, ash about 0.5% and fat about 0.15%. Whey protein (total nitrogen times 6.38) is present at under 1%.

The process of the invention preferably employs bovine whey, preferably as deproteinized whey. The term "deproteinized whey" refers to the liquid remaining after treatment of whey to remove the majority of the whey protein. The material is not deproteinized completely, but contains most of the insoluble membrane protein fragments from MFGM originally present in the whey in addition to residual whey, lactose, salts and other proteins. The invention utilizes, preferably, deproteinized whey obtained after removal of the major whey proteins by known industrial processing, such as filtration, ion-exchange chromatography, and the like. This fraction contains most of the insoluble membrane fragments which contain protein and associated fat. Among the materials present with the MFGM are glycomacropeptides (GMP), which in one facet of the invention can be separated from the glycoproteins and recovered, if desired.

Considerable amounts of MFGM fractions still exist in whey after removing fat and casein. The MFGM fractions not adsorbed to the resin are concentrated on a microfiltration (MF) membrane and diafiltrated with water. This retentate fraction contains most of the insoluble membrane fragments and some GMP (see lane 2 of FIG. 1), although majority of GMP is in the permeate of microfiltration. About 64% of the fraction are proteins and about 27% are fat.

Reference to FIG. 5 shows a flow diagram of a process for isolating and recovering a dried glycoprotein fraction. According to the process, glycoproteins are recovered from whey, such as deproteinized whey. In a first step, the whey is micro-filtered to remove large molecules and aggregates. Typically, the microfiltration unit will be of the type having a molecular weight cut off from 500K Daltons to the pore size of $0.5\mu$. The resulting micro filtered deproteinized whey is then preferably diluted to facilitate further processing. Typical dilutions will be to achieve total protein (TP, total nitrogen times 6.38) contents of under about 10%, e.g., from 2 to 5%, with 3% being preferred and exemplified below.

The resulting diluted aqueous microfiltered deproteinized whey protein from the above or other processing is heated to coagulate residual whey protein. This can be accomplished in any suitable manner, say heating up to about 100° C. for a time effective to coagulate the majority of the whey proteins. Typical times will be from 1 to 60 minutes and temperatures will typically be within the range of from 80° to 100° C., e.g., about 90° C. The resulting heated solution is then cooled sufficiently to precipitate coagulated whey protein. The preparation can then be completed by centrifuging the resulting cooled solution and separating resulting supernatant containing glycoproteins from fat and precipitated whey protein. The process of FIG. 5 is illustrated in Example 1.

Figure 4:
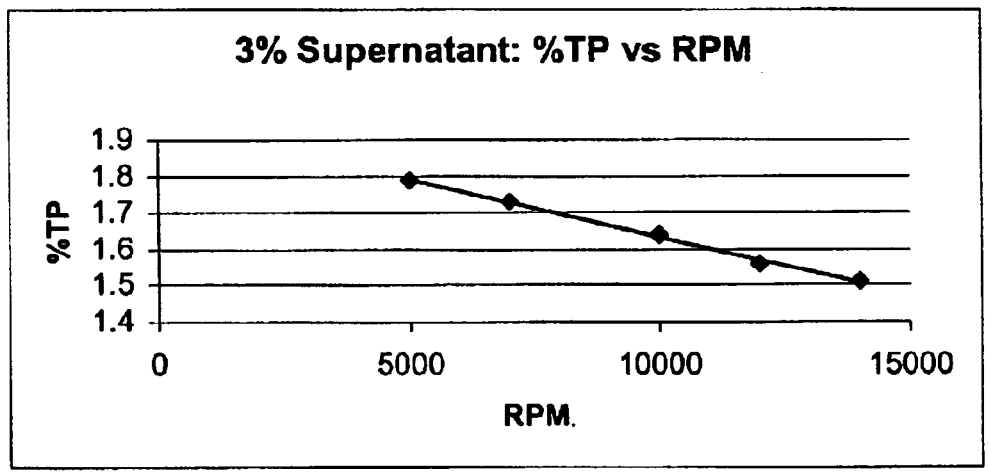
FIG. 4 is a graph showing the effect of centrifugation rate (RPM) on percent total protein (TP) in a supernatant of the type processed in Example 2.

The centrifugation is important to separate out fat and proteins other than the glycoprotein. To illustrate the effect of centrifugation on processing in accord with the invention, a series of trials was run. In each, 289 g of MF concentrate from Example 1 (below) was diluted by using 1% sodium chloride to 3% total protein (TP). The solution was heated to 92° C. for 30 minutes, and then cooled down to 4° C. in the ice water bath. The resulting cooled solution was then placed in a Beckman J2-21 centrifuge and processed at various radial speeds (proportional to G forces) at 4° C. FIG. 4 shows that the percent TP in the supernatant (glycoprotein fraction) decreases linearly with the increasing of G force. In addition, FIG. 4 shows that the percent fat in the supernatant (glycoprotein fraction) also linearly decreases with the increasing G force. These two figures indicate that a glycoprotein fraction of highest purity can be from the higher G forces. Accordingly, centrifugation at the corresponding G forces, for times of from about 1 to about 60 minutes is appropriate.

Figure 7:
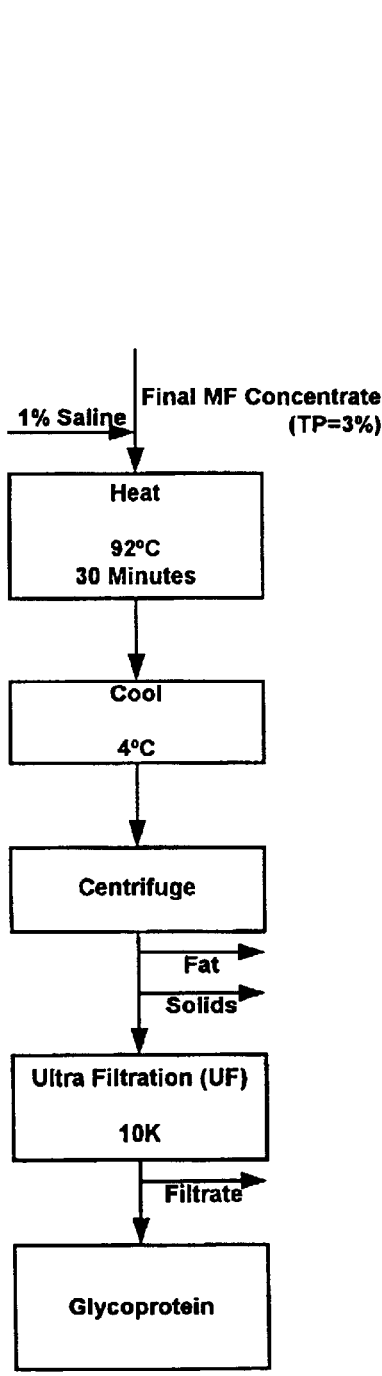
FIG. 7 is a flow diagram of a process for isolating and recovering a liquid glycoprotein fraction that can be sterilized.

The product glycoprotein concentrate can be dried, such as by freeze drying or spray drying, or recovered and stored in liquid form as, for example, illustrated in the processes of FIGS. 6 and 7. In the process of FIG. 6 (exemplified in Example 2) a liquid glycoprotein fraction is recovered. In the process of FIG. 7, saline is employed to dilute the microfiltered concentrate prior to heating to improve the recovery of a liquid glycoprotein fraction that can be sterilized, such as by autoclaving. It is an advantage of the invention that the products can thus, be preserved without the need for a antimicrobial additive, if desired Preferred liquid products of the invention will be stable for at least one month, preferably at least six months, when packaged and stored. Also, preferred products are crystal clear, showing no observable sediment or cloud. The procedure of FIG. 7 (exemplified in Example 3) produces products that can be easily autoclaved with good product stability and clarity. The products of that process can be autoclaved after sealing in packages to assure that each package is sterile. And, this can be done without degrading the product. Preferably, the supernatant is stable to autoclaving and free of visible separation and/or sedimentation after storage in a sealed container at 20° C. for a period of at least one month. In addition, aseptic packaging methods can be employed.

Figure 8:
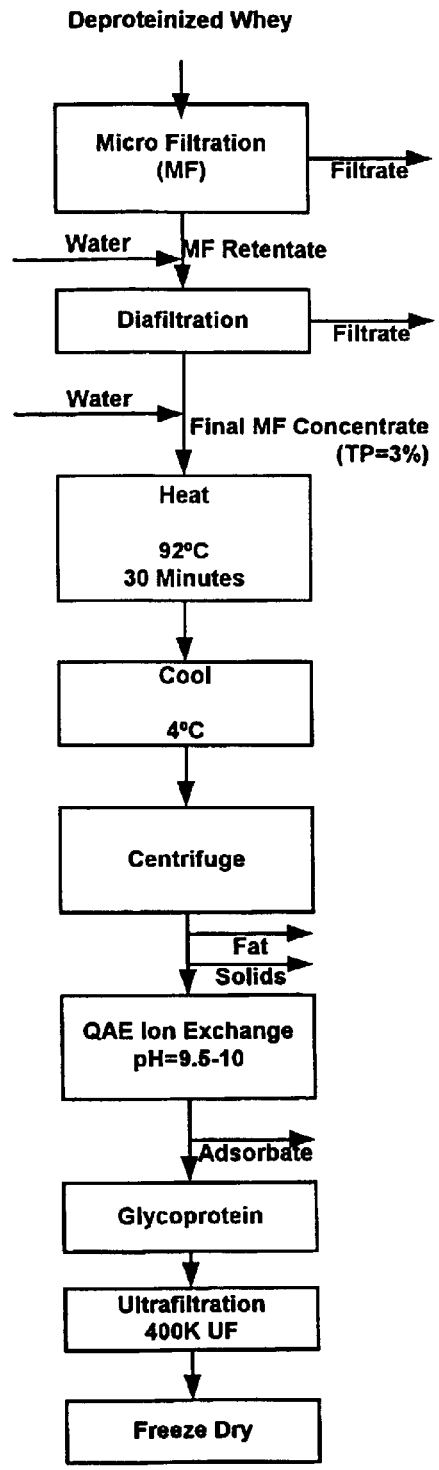
FIG. 8 is a flow diagram of a process for isolating and recovering a glycoprotein fraction free of a majority of glycomacropeptides (GMP).

FIG. 8 is a flow diagram of a process (exemplified in Example 4) for isolating and recovering a glycoprotein fraction free of a majority of GMP. Here, the supernatant is adjusted to alkaline pH and then subjected to ion exchange extraction to separate a glycomacropeptide fraction.

The following examples are presented to further illustrate and explain the invention and are not to be taken as limiting in any regard. Unless otherwise indicated, all parts and percentages are by weight. Total protein values (TP) are based on total nitrogen (total nitrogen times 6.38).

EXAMPLE 1
Isolation of Glycoproteins from Whey, Dry

A quantity of deproteinized whey was concentrated on an MF membrane and diafiltrated with water. The retentate was diluted with distilled water to a total protein of 3%. The diluted solution was heated in a water bath with temperature of 80–92° C. for 20 minutes while stirring. The solution was then cooled in a cold water bath and centrifuged at 10,000 rpm at 4° C. for 30 minutes. This procedure coagulates whey protein, while maintaining lactose, salts and other minor impurities in solution. The top fat layer is removed to the extent possible. The supernatant is collected and has a total protein of about 2%. The process eliminated most of the non-glycoproteins and a small amount of glycoproteins. A majority of the proteins in the supernatant were identified as glycoproteins as shown by SDS-PAGE stained with PAS-followed by Coomassie blue (lane 3 of FIG. 1). Most of the proteins precipitated were non-glycoproteins (lane 4 of FIG. 1). The supernatant was concentrated by UF membrane to a TP of 13% and freeze-dried.

EXAMPLE 2
Isolation of Glycoproteins from Whey, Solution

Figure 2:
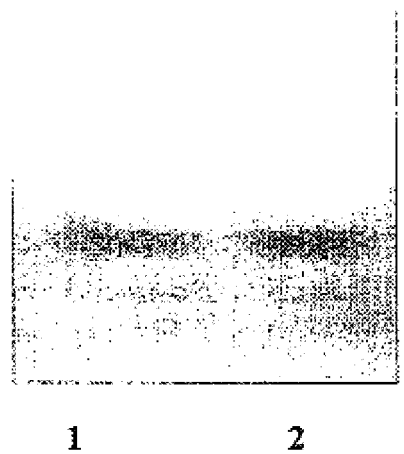
FIG. 2 is again a photograph of slide panels showing SDS PAGE electrophoresis, PAS stained samples utilizing 4–15% gradient gels indicating the presence of glycoproteins. Lanes 1 and 2 are the results for glycoprotein preparations from Examples 2 and 3, respectively.
Figure 3:
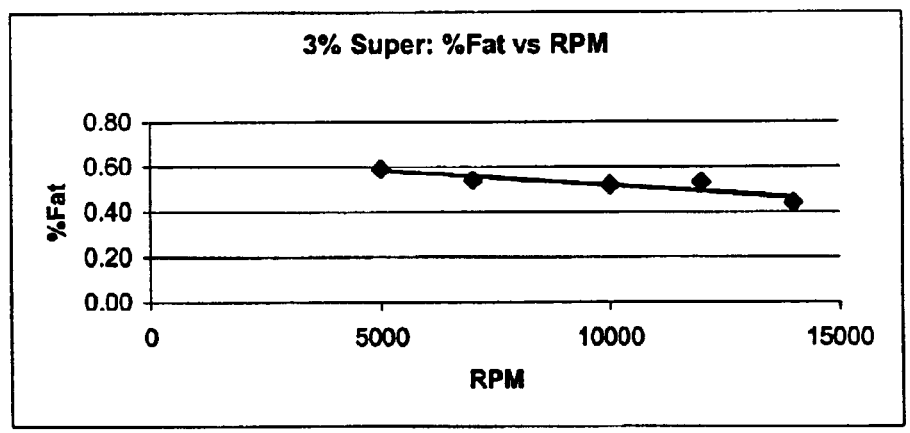
FIG. 3 is a graph showing the effect of centrifugation rate (RPM) on percent fat in a supernatant of the type processed in Example 2.

Concentrated deproteinized whey (62.6 kg) obtained as in Example 1 was processed by using 0.1 micron microfiltration membrane. Reverse osmosis (RO) water was added into the MF retentate to filter the lactose and small molecular material out by diafiltration processing. A final 7.13 kg of MF concentrate was collected. The TP, total solid (TS) and fat in the final MF concentrate were 15.6%, 22% and 3.4% respectively. Of the final MF concentrate, 1060 g was diluted by distilled water to a TP of 3%. The diluted protein solution was heated to 92° C. for 30 minutes. The solution was then cooled to 4° C. and placed in a Beckman J2-21 Centrifuge at a G force of 20000 for 60 minutes at 4° C. The top fat layer was carefully removed and the supernatant was further separated from the precipitate on the bottom. The collected supernatant was processed by using a 10 K ultrafiltration membrane to concentrate the glycoprotein fraction. A final 600 g glycoprotein faction from the 10 K UF membrane was obtained. The TP, TS and fat were 8.7%, 13.3% and 4.67% respectively. See FIG. 2, the lane on the left, lane 1.

EXAMPLE 3
Isolation of Glycoproteins from Whey, Saline Solution

A 1019 g portion of MF final concentrate from the Example 1 was diluted by 1% sodium chloride solution to 3% of total nitrogen protein. The protein solution was heated to 92° C. for 30 minutes, and then was cooled down to 4° C. The Beckman J2-21 Centrifuge was employed to separate the glycoprotein fraction. The top fat layer was carefully removed, and the supernatant separated from the precipitate at the bottom. The collected supernatant was processed by using a 10K membrane to concentrate the glycoprotein fraction and diafiltrated to remove the excess minerals and lactose. A final 688 g of the 10K-membrane concentrate glycoprotein fraction was obtained. The TP, TS and fat in the final concentrated were 7.44%, 11.74% and 2.12% respectively. See FIG. 2, the lane on the right, lane 2.

EXAMPLE 4
Isolation of Glycoproteins from Whey, Reduced GMP

A portion of the MF Retentate from Example 1 was diluted to 3% TP and the pH was adjusted to 8.2. The resulting solution was heated to about 90° C. for 20 minutes and cooled in cold water. It was centrifuged as in Example 1 and the supernatant containing GMP collected. The pH of supernatant was adjusted to 9.5–10 and the solution was then reacted with QAE ion exchange resin for 30 minutes to remove GMP. The fraction that was not adsorbed was collected and diafiltrated with a 400K UF membrane. The concentrated membrane retentate was freeze dried. In FIG. 1, Lane 5 of the SDS gel shows this prep, and lane 6 shows the adsorbed fraction eluted with 1M NaCl.

Characterization by Gel Electrophoresis

Reference to FIG. 1 shows 4–15% SDS PAGE of glycoprotein preparations.

Panel A and B are same gel which was stained first with PAS staining (A) and later with Coomassie blue (B). Lane 1, shows molecular weight standards, from top: 205, 121, 70, 52, 34, 29, 16, 7 kd; lane 2, MF diafiltrated MFGM fraction as stated in Example 1; lane 3, glycoprotein preparation as stated in Example 1; lane 4, precipitates of MFGM fraction after heating to 92° C. as stated in Example 1; lane 5, glycoprotein preparation as stated in Example 4; lane 6, 1M sodium chloride eluate of QAE adsorbed proteins as stated in Example 4.

On SDS gel, by comparison with published information, the glycoprotein preparation from Example 1 in lane 3 may contain the following glycoproteins: MUC1, PASIII, CD36, PAS 6/7, GMP, and small amounts of non-glycoproteins such as beta-lactoglobulin, alpha-lactalbumin and xanthine dehydrogenase/oxidase. Comparing with the MFGM fraction from Example 1 in lane 2, there were much less non-glycoproteins in glycoprotein preparation of Example 1 (lane 3). MUC1 and PAS III cannot be stained with Coomassie blue (CB) and CD36, PAS 6/7 and GMP can be stained by both PAS- and CB. The top two bands ranging in molecular weights of 160 k to 190 k were MUC1. The PAS band with molecular weight of around 100 k was possibly PAS III. The band below PAS III band, with approximate molecular weight of 76 k, was probably CD36. There were one to two faint bands with molecular weights around 48 k that might be PAS III. The major glycoprotein (or glycopeptide) band on lane 3 was probably GMP which always appeared on 4–15% gradient SDS-gel a molecular weight of 31 k, much larger than the theoretical molecular weight of 8 k for GMP. The preparation of Example 1 passed through QAE resin in example 4 removed most of the soluble GMP. However, there was still a heavy glycoprotein band at that position, this is probably an unknown glycoprotein other than the GMP, which might be associated with MFGM.

Composition Comparisons of the Samples

The freeze-dried samples from Examples 1 and 4 were analyzed for chemical composition as shown in Table 1.

Amino acid composition analyses for the glycoprotein Example 1 and Example 4 were performed. The two samples are rich in threonine, glutamic acid/glutamine, and serine. Table 2 shows a comparison of amino acid compositions (expressed as mole percentage) of commercial sweet dairy whey with that of our glycoprotein preparations from Examples 1 and 4. The amino acid profiles for the two glycoprotein preparations are similar in that they both were rich in threonine and serine, which are typical of glycoproteins because glycosylations occur at some of these sites.

Between the two preparations, the one of Example 4 had more phenylalanine, which means less GMP was present because GMP contains no phenylalanine.

From the gel electrophoresis and composition analysis results, we conclude that the two preparations in Examples 1 and 4 are new glycoprotein products from new preparation methods.

TABLE 1

Chemical Compositions of Samples of MFGM as Prepared and Products from Examples 1 and 4 (Expressed as weight percentage)

|  | MFGM Retentate | Glycoprotein, Example 1 | Glycoprotein, Example 2 |
| --- | --- | --- | --- |
| Total Protein | 64 | 67 | 56 |
| Fat | 27 | 21 | 33 |
| Moisture | 1.7 | 5.9 | 3.2 |
| Ash | 3 | 3.4 | 3.4 |

TABLE 2

Amino Acid Compositions of Bovine Milk Glycoprotein, Examples 1 and 4
(Values are expressed as mole percentage of amino acids recovered)

| Amino acid | Glycoprotein, Example 1 | Glycoprotein, Example 2 | Sweet Dairy Whey |
| --- | --- | --- | --- |
| Serine | 11.2 | 11.4 | 7.1 |
| Proline | 9.52 | 6.24 | 6.6 |
| Threonine | 14.7 | 12 | 8.4 |
| Alanine | 5.95 | 6.24 | 7.9 |
| Glutamic acid/Glutamine | 15.3 | 12.5 | 17.1 |
| Leucine | 4.78 | 10.4 | 10.7 |
| Glycine | 3.32 | 5.47 | 3.2 |
| Aspartic acid/Asparagine | 9.28 | 9.36 | 11.2 |
| Valine | 5.79 | 6.12 | 6.0 |
| Isoleucine | 6.23 | 5.32 | 5.66 |
| Arginine | 2.31 | 3.21 | 0.75 |
| Lysine | 7.83 | 7.24 | 6.92 |
| Methionine | 0.6 | 2.16 | 0.8 |
| Phenylalanine | 1.48 | 3.65 | 2.1 |
| Histidine | 1.19 | 2.53 | 1.15 |
| Tyrosine | 0.49 | 2.20 | 0.3 |

The above description is intended to enable the person skilled in the art to practice the invention. It is not intended to detail all of the possible modifications and variations which will become apparent to the skilled worker upon reading the description. It is intended, however, that all such modifications and variations be included within the scope of the invention which is seen in the above description and otherwise defined by the following claims. The claims are meant to cover the indicated elements and steps in any arrangement or sequence which is effective to meet the objectives intended for the invention, unless the context specifically indicates the contrary.

What is claimed is:

1. A process for preparing mucin enriched glycoproteins from bovine whey, comprising:

diluting microfiltered deproteinized whey protein;

heating the resulting diluted aqueous micro-filtered deproteinized whey protein to coagulate whey protein;

cooling the resulting heated solution to precipitate coagulated whey protein;

centrifuging the resulting cooled solution and separating resulting supernatant containing glycoproteins from fat and precipitate.

2. A process according to claim 1 wherein the cooled solution is subjected to centrifugation for from 1 to 60 minutes.

3. A process according to claim 1 wherein the microfiltered deproteinized whey protein is diluted to a protein content of about 1–10% prior to heating.

4. A process according to claim 1 wherein the supernatant has a total protein content of from about 0.5 to 5%.

5. A process according to claim 1 wherein the supernatant is adjusted to alkaline pH and then subjected to ion exchange extraction to separate a glycomacropeptide fraction.

6. A process according to claim 1 wherein the supernatant is dried to recover the glycoproteins in dry form.

7. A process according to claim 6 wherein the dried glycoproteins are resuspended and autoclaved.

8. A process according to claim 1 wherein the supernatant is recovered as a solution.

9. A process according to claim 1 wherein the microfiltered deproteinized whey protein is diluted with a saline solution prior to heating.

10. A process according to claim 8 wherein the supernatant is recovered as a stable saline solution.

11. A process according to claim 8 wherein the supernatant is autoclaved.

12. A process according to claim 11 wherein the supernatant is filled into a sealed package prior to autoclaving.

13. A process according to claim 1 wherein the supernatant is stable to autoclaving.

14. A process according to claim 1 wherein the supernatant is stable to storage for a period of at least one month.

15. A process according to claim 1 wherein the supernatant is free from visible cloud.

16. A process according to claim 11 wherein the supernatant is stable to storage for a period of at least one month.

17. A process according to claim 1 wherein the supernatant is stable to autoclaving and free of separation after storage in a sealed container at 20° C. for a period of at least one month.

* * * * *